(12) United States Patent
Stakenborg et al.

(10) Patent No.: US 11,220,706 B2
(45) Date of Patent: Jan. 11, 2022

(54) COMBINED EXTRACTION AND PCR SYSTEMS

(71) Applicant: IMEC VZW, Leuven (BE)

(72) Inventors: Tim Stakenborg, Heverlee (BE); Paolo Fiorini, Brussels (BE)

(73) Assignee: IMEC vzw, Leuven (BE)

( * ) Notice: Subject to any disclaimer, the term of this patent is extended or adjusted under 35 U.S.C. 154(b) by 255 days.

(21) Appl. No.: 16/448,713

(22) Filed: Jun. 21, 2019

(65) Prior Publication Data

US 2019/0309346 A1    Oct. 10, 2019

Related U.S. Application Data

(63) Continuation-in-part of application No. PCT/EP2017/083681, filed on Dec. 20, 2017.

(30) Foreign Application Priority Data

Dec. 23, 2016   (EP) .................................... 16206816

(51) Int. Cl.
*C12Q 1/6806*    (2018.01)
*B01L 3/00*    (2006.01)
*B01L 7/00*    (2006.01)
*C12Q 1/686*    (2018.01)

(52) U.S. Cl.
CPC .......... *C12Q 1/6806* (2013.01); *B01L 3/5027* (2013.01); *B01L 3/502715* (2013.01); *B01L 7/52* (2013.01); *C12Q 1/686* (2013.01); *B01L 3/502746* (2013.01); *B01L 3/502761* (2013.01); *B01L 2200/0631* (2013.01); *B01L 2200/0647* (2013.01); *B01L 2300/0867* (2013.01); *B01L 2300/0883* (2013.01); *B01L 2300/0896* (2013.01); *B01L 2300/161* (2013.01); *B01L 2400/0406* (2013.01); *B01L 2400/086* (2013.01); *C12Q 2531/113* (2013.01); *C12Q 2600/16* (2013.01)

(58) Field of Classification Search
CPC .. C12Q 1/6806; C12Q 1/686; C12Q 2600/16; C12Q 2531/113; C12Q 2547/101; C12Q 2563/159; C12Q 2565/629; B01L 3/5027; B01L 7/52; B01L 2200/0631; B01L 2300/0883; B01L 2300/0896
See application file for complete search history.

(56) References Cited

U.S. PATENT DOCUMENTS

2008/0171366 A1    7/2008 Cheong et al.
2009/0186357 A1    7/2009 Mauk et al.
2009/0266421 A1 *   10/2009 Linder ............... B01L 3/502784
                                                               137/1
2011/0220502 A1    9/2011 Selden et al.
2014/0194313 A1    7/2014 Craighead et al.
2015/0151301 A1    6/2015 Fiorini et al.

FOREIGN PATENT DOCUMENTS

| CN | 105296349 A | 2/2016 |
| EP | 2896457 A1 | 7/2015 |
| WO | 2012/136400 A1 | 10/2012 |
| WO | 2012/170560 A2 | 12/2012 |
| WO | 2012/170560 A3 | 12/2012 |
| WO | 2013/126714 A2 | 8/2013 |
| WO | 2015/160863 A1 | 10/2015 |

OTHER PUBLICATIONS

Cai, Qing et al., "Ultra-Fast, Sensitive and Quantitative On-Chip Detection of Group B Streptococci in Clinical Samples", Talanta, vol. 192, 2019, pp. 220-225.
Powell, Laura et al., "Rapid and Sensitive Detection of Viral Nucleic Acids Using Silicon Microchips", Analyst, vol. 143, 2018, pp. 2596-2603.
Cohen, Dawn E. et al., "Self-Digitization of Sample Volumes", Anal. Chem. vol. 82, 2010, pp. 5707-5717.
Dube, Simant et al., "Mathematical Analysis of Copy Number Variation in a DNA Sample Using Digital PCR on a Nanofluidic Device", PLoS ONE, vol. 3, No. 8, Aug. 2008, pp. 1-9.
Lu, Chang et al., Diffusion-Based Microfluidic PCR for "One-Pot" Analysis of Cells, Lab On A Chip, vol. 14, No. 16, Aug. 21, 2014, 3 pages.
Lui, Clarissa et al., "Nucleic Acid-Based Detection of Bacterial Pathogens Using Integrated Microfluidic Platform Systems", Sensors, vol. 9, 2009, pp. 3713-3744.
Davies, Ryan T. et al., "Microfluidic Filtration Systems to Isolate Extracellular Vesicles from Blood", Lab on a Chip, vol. 12, 2012, pp. 5202-5210.
European Search Report, European Patent Application No. 16206816.7 dated Apr. 25, 2017, 10 pages.
PCT International Search Report and Written Opinion, PCT International Application No. PCT/EP2017/083681, dated Mar. 29, 2018, 14 pages.

* cited by examiner

*Primary Examiner* — David C Thomas
(74) *Attorney, Agent, or Firm* — McDonnell Boehnen Hulbert & Berghoff LLP

(57) ABSTRACT

The disclosure provides methods and systems for analyzing fluid samples comprising obtaining fluid samples in at least one cavity of a substrate and introducing also buffers and/or reagents in the cavity, performing nucleic acid extraction and/or purification in the cavity, and performing nucleic acid amplification in the same cavity.

20 Claims, 19 Drawing Sheets

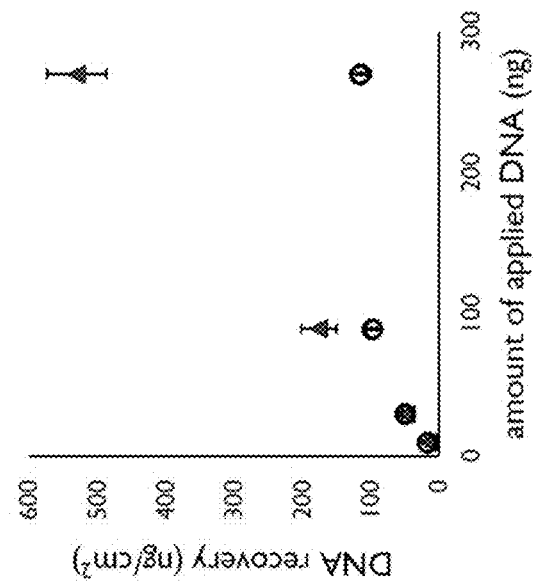
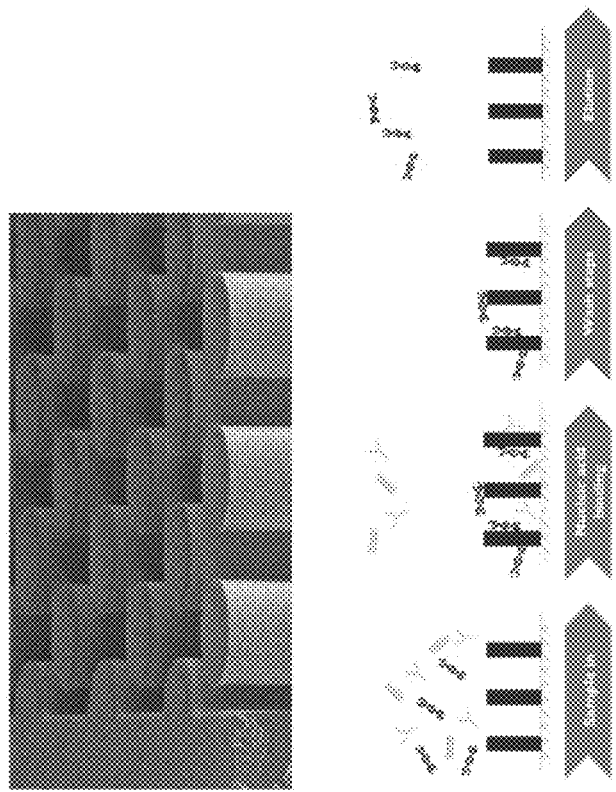
FIG. 19

COMBINED EXTRACTION AND PCR SYSTEMS

CROSS-REFERENCE TO RELATED APPLICATIONS

The present application is a continuation-in-art application claiming priority to International Application No. PCT/EP2017/083681, filed Dec. 20, 2017, which claims priority to European Application No. EP 16206816.7, filed Dec. 23, 2016, the contents of each of which are hereby incorporated by reference in their entireties.

FIELD OF THE DISCLOSURE

The disclosure relates to the field of sample characterization. More specifically it relates to methods and systems for performing characterization of a fluid sample using PCR.

BACKGROUND

Genetic information is encoded in nucleic acids. Genetic studies, such as antibiotic resistance detection, oncology studies, diagnosis, genetic engineering, criminology, and others usually require detection of specific fragments of nucleic acid. Thus, it is necessary to extract the nucleic acid from its container/carrier (e.g., a virus, a cell, or a nucleus).

Extraction typically uses filters or bead-based protocols in a series of steps involving, for example, lysis (i.e., opening cells), clumping or aggregating lipids and proteins, and separating the nucleic acid from the aggregated material, among other steps. Once the nucleic acid is extracted, it can be introduced into an analysis unit. These units are traditionally large and comprise large heating blocks, and potentially cartridges, channels, disposable plastics, etc.

Microelectronics, semiconductor processing, and nanotechnology allows production of small, portable devices called lab-on-chip systems, which enable point-of-care testing in which the sample does not need to be displaced to an analysis unit in, for example, a central analysis lab, but rather in which the analysis unit can be displaced to a patient, saving time and allowing for more continuous monitoring.

The detection of specific sequences of nucleic acid associated with a particular study (e.g., detection of particular types of DNA damage or mutation, microorganisms, viruses, and/or strains thereof) generally requires amplification. Thus, firstly the part of interest of the long nucleic acid molecule is identified, then it is replicated (amplified) by a technique known as polymerase chain reaction (PCR).

This technique, however, has several limitations. For example, standard PCR techniques are sensitive to many components and substances and in order to generate reproducible, e.g., matrix-independent, results, the nucleic acids typically need to be purified before amplification. Standard PCR techniques also do not allow for easy correlation between nucleic acid fragments and single carrier (e.g., exosome, virus, bacterium, cell, etc.). This would require dedicated equipment to individually isolate genetic carriers and extensive sample preparation and extraction steps, which increase costs and delays the production of results.

SUMMARY

It is an object of embodiments of the present disclosure to provide a compact device and simple method to provide extracted and/or purified nucleic acid and provide accurate nucleic acid amplification, and to provide devices and methods for performing PCR, e.g., time-saving PCR and/or PCR.

The present disclosure relates to a method for analyzing a fluid sample, the method comprising obtaining the fluid sample in at least one cavity of a substrate and introducing also buffers and/or reagents in the cavity, performing nucleic acid extraction and/or purification in the cavity, and performing nucleic acid amplification in the same cavity. The cavity comprises a silicon-based pillar filter. Pillars may be grown or etched in the substrate so that they are an integral part of the structure forming the cavity. The silicon-based pillar filter may comprise silicon pillars. Silicon-based pillars also may include silicon oxide pillars, or alike. The pillars furthermore may be coated, such as for example coated with different oxides such as one or more $SiO_2$ and/or $HfO_x$, etc.

In some embodiments, obtaining a fluid comprises obtaining a diluted fluid. In some embodiments of aspects of the present disclosure, lab-on-chip systems can be obtained in which both nucleic acid extraction and/or purification and amplification can be performed in the same cavity. In some embodiments, a simplified work flow can be obtained compared to conventional systems. In some embodiments, the overall chip footprint can be small, e.g., reduced compared to conventional lab-on-chip systems. The method thus may be adapted for not performing an elution step between performing nucleic acid extraction and performing nucleic acid amplification.

In some embodiments, the obtaining of the fluid sample in at least one cavity or a plurality of cavities comprises obtaining the fluid sample in the at least one cavity or a plurality of cavities comprising a plurality of micropillar structures. In some embodiments, by using solid phase micropillars, a large surface to volume ratio is obtained. The one or more cavities may have a surface to volume ratio as such that the diffusion time to the surface is smaller than the overall assay time. To increase the surface to volume ratio, e.g., pillars can be introduced. Alternatively, or in combination therewith, the maximum diffusion distance from solution to cavity/pillar surface can be selected to be small enough so as to reduce the diffusion time, e.g., 10 µm or smaller.

In some embodiments, when multiple cavities are used, changes in relative gene expression occurring in individual cells can be detected since the gene expression levels will not be averaged out over the entire population of cells. Furthermore, by parallelization, expression profiles of single cells can be analyzed in high throughput. In some embodiments, multiplexed, quantitative detection of bacteria, together with their specific antibiotic markers, can be obtained. This results in the possibility of antibiotic resistance screening whereby correlation is allowed between the detected pathogens and resistance markers, in view of the direct linkage between observed antibiotic resistance and pathogens. Furthermore, embodiments of the present disclosure allow for absolute quantification such that a positive pathogen detection can be correlated with clinical relevance.

In some embodiments, the obtaining of the fluid sample in one or more cavities comprises obtaining a diluted fluid sample in a plurality of cavities, and the method may comprise, for each cavity, performing the nucleic acid extraction and/or purification in the cavity and subsequently performing nucleic acid amplification in the same cavity.

In some embodiments, no separate sample preparation step is required prior to the dilution step. In some embodiments, when multiple cavities are used, and when having a bulk mix of DNA fragments, these can be traced back to their original carrier. In some embodiments, generic targets from the same origin, i.e., from the same genetic carrier such as a cell, exosome, virus, bacteria, or the like, will be physically constrained to the same cavity. As such, genetic correlation (linkage) between different fragments (i.e., targets) can be easily obtained using multiplexed PCR. This directly enables a plethora of applications that are very difficult or close to impossible to obtain with current state of the art methodologies (some examples are given above). Indeed, using standard state of the art technologies, nucleic acid extraction and/or purification is performed as a separate sample preparation step prior to amplification. As explained, extraction and/or purification on such standard samples (containing, e.g., numerous genetic carriers such as cells) will yield a mix of nucleic acids. Starting from such a standard sample, only bulk measurements can be performed and all information about targets originating from, e.g., a single cell, chromosome, or genetic carrier is gone. In sharp contrast to these bulk measurements, embodiments of the present disclosure allow genetic linkage or correlation between different DNA/RNA targets directly, as well as quantification thereof.

In some embodiments, the proposed protocol does not require to have dedicated equipment to individually isolate genetic carriers (e.g., exosome, virus, bacterium, cell etc.) as this can be done based on simple dilution.

In some embodiments, obtaining the fluid sample comprises providing a predetermined volume of fluid containing nucleic acid carriers per cavity, for obtaining an average of less than a nucleic acid carrier per cavity. In some embodiments, genetic correlation between different targets originating from, e.g., a single cell, chromosome, or genetic carrier and quantification can be obtained.

In some embodiments, obtaining the fluid sample comprises providing a volume of less than 10 nanoliter per cavity. The latter typically may be applied when a plurality, e.g., more than 50 cavities, are used.

The present disclosure also relates to a microfluidics system adapted for analyzing a fluid sample, the system comprising a substrate comprising at least one cavity, an input for introducing a fluid sample in the cavity, the at least one cavity further comprising a surface adapted to provide nucleic acid extraction, and a controller for inducing in the cavity nucleic acid extraction conditions for inducing nucleic acid extraction in the cavity and subsequently inducing nucleic acid amplification conditions for inducing nucleic acid amplification in the same cavity. The at least one cavity also comprises a silicon-based pillar filter. In some embodiments, the silicon-based pillar filter comprises a plurality of micropillar structures. In some embodiments, the silicon-based pillar filter comprises silicon pillars. In some embodiments, the controller is programmed for not performing an elution step between performing nucleic acid extraction and performing nucleic acid amplification.

In some embodiments, nucleic acid extraction and/or purification and PCR can be sequentially performed in the same cavity without sample transfer. In some embodiments, a compact microfluidics system allowing PCR analysis can be obtained. In some embodiments, a system readily integratable in a lab-on-chip system is obtained.

In some embodiments, the one or more cavities comprise a micropillar array. In some embodiments, an increase surface area for nucleic acid extraction and/or purification is obtained.

In some embodiments, digital PCR (dPCR) can be obtained.

Each of the cavities may have a maximum capacity of 10 nanoliters. In some embodiments, a single cavity may include, at most, only one or very few nucleic acid carriers.

In some embodiments, the surface of the one or more cavities comprises silicon oxide.

In some embodiments, the substrate comprises at least one trench for thermally isolating the one or more cavities. In some embodiments, well-known binding procedures and buffers can be used. In some embodiments, the influence of the PCR reaction on nearby electronics and other cavities, reactors, and/or microfluidic channels is reduced, and in turn the cavity is isolated from external influences.

In some embodiments, the system is adapted to further provide capillary pumping.

In some embodiments, the system comprises a mixer for mixing buffers and/or reagents.

In some embodiments, the system comprises a heater for adjusting the temperature in the cavity.

In some embodiments, the system comprises a temperature sensor to measure the temperature of the cavity. In some embodiments, extra pumps are not needed in the microfluidics system. In some embodiments, a compact PCR or dPCR system can be obtained with good temperature control. In some embodiments, the system can be integrated in a microfluidics platform for a lab-on-chip device, allowing point-of-care testing.

In one aspect, the present disclosure provides a method for analyzing a fluid sample, the method comprising obtaining a diluted fluid sample in a plurality, e.g., an array, of cavities of a substrate, introducing buffers and/or reagents, performing nucleic acid extraction and/or purification, and performing nucleic acid amplification in the cavities, and applying a PCR analysis for the plurality of cavities for determining a concentration of a target in the fluid sample. In some embodiments, the extraction and/or purification and amplification optionally can be done in the same cavity. Nevertheless, the extraction and/or purification can optionally also be performed in a cavity on the same substrate different than the cavity wherein amplification is performed. When the extraction and the amplification is performed in the same cavity, the method also may comprise linking the obtained nucleic acid marker with individual bio-vesicles. The method also may comprise identifying with a characterization technique the individual bio-vesicles.

The PCR performed may be digital PCR but is not limited thereto. In some embodiments, the PCR is qPCR. In one example, if one would look at differential expression of single cells in each cavity, one could for example perform a qPCR analysis and, for example, determine the Ct value per cavity.

In some embodiments, obtaining the fluid sample comprises providing a predetermined volume of fluid containing nucleic acid carriers per cavity, for obtaining an average of less than a nucleic acid carrier per cavity.

In some embodiments, obtaining the fluid sample comprises providing a volume of less than 10 nanoliter per cavity.

In some embodiments, obtaining the fluid sample in a plurality of cavities comprises obtaining the fluid sample in the plurality of cavities comprising a plurality of micropillar structures.

In a related aspect, the present disclosure provides a microfluidic system for analyzing a fluid sample, the microfluidic system comprising a substrate comprising a plurality of cavities, and an input for introducing a fluid sample in the cavities, a controller for inducing nucleic acid extraction and/or purification and for inducing nucleic acid amplification in the cavities, and a processor programmed for performing a PCR analysis based on the plurality of cavities. In some embodiments, for each of the cavities, both extraction and/or purification and the amplification may be performed in one and the same cavity. Such systems may be advantageously used for linking nucleic acid markers with individual bio-vesicles.

The cavities may comprise a surface adapted to provide nucleic acid extraction and wherein the controller is adapted for inducing in the same cavity extraction and, subsequently, amplification for each of the cavities.

Each of the cavities may have a maximum capacity of 10 nL.

A surface of the plurality of cavities may comprise silicon oxide and/or wherein the substrate may comprise at least one trench for thermally isolating the plurality of cavities.

In some embodiments, the system is adapted to further provide capillary pumping and/or wherein the system comprises a mixer for mixing buffers and/or reagents.

In some embodiments, the system comprises a heater for adjusting the temperature in the cavities.

The present disclosure provides a diagnostic device comprising a microfluidics system as described above in one of the aspects. The diagnostic device may be a lab-on-chip device, may be a chip-based device used in a larger system, or may be a system not being chip-based.

The present disclosure further provides the use of a system as described above in one of the aspects for screening antibiotics resistance or for identifying relative changes in gene expression or for linking multiple nucleic acids targets to a single genetic carrier.

Particular and preferred aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

BRIEF DESCRIPTION OF THE FIGURES

The above, as well as additional, features will be better understood through the following illustrative and non-limiting detailed description of example embodiments, with reference to the appended drawings.

FIG. 19 shows the extraction at silicon-based micropillars, illustrating features of example embodiments of the present disclosure.

Figure 1:
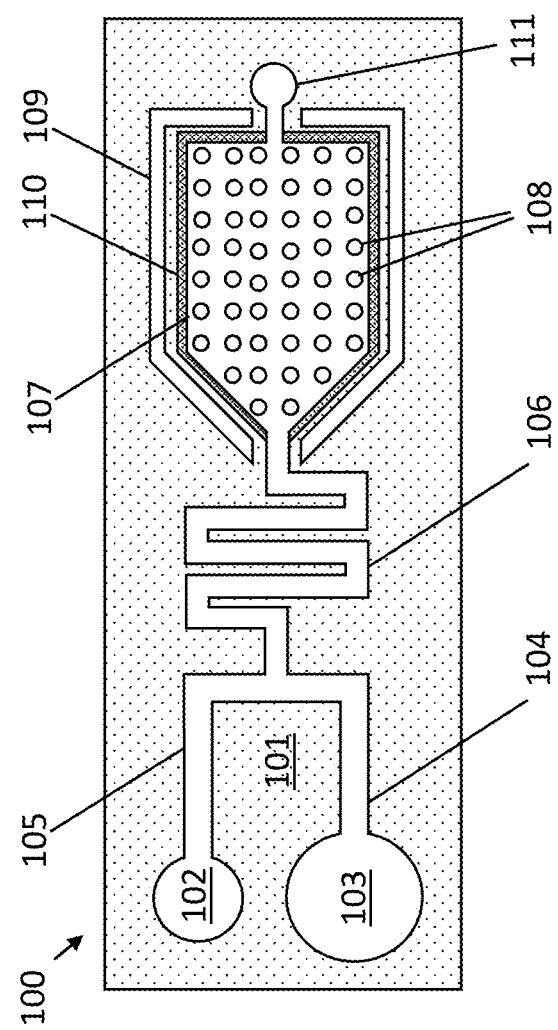
FIG. 1 illustrates a microfluidics platform with a cavity for combined extraction and/or purification/PCR according to example embodiments of the present disclosure.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

The present disclosure will be described with respect to particular embodiments and with reference to certain drawings but the present disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the present systems and methods.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the present disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the present disclosure described herein are capable of operation in other orientations than described or illustrated herein.

It is to be noticed that the term "comprising," used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in some embodiments," "in one embodiment," or "in an embodiment" in various places throughout this specification are not necessarily all referring to the same embodiment, but may. Furthermore, the particular features, structures, or characteristics may be combined in any suitable manner, as would be apparent to one of ordinary skill in the art from this disclosure, in one or more embodiments.

Similarly, it should be appreciated that in the description of exemplary embodiments, various features of the present disclosure are sometimes grouped together in a single embodiment, figure, or description thereof for the purpose of streamlining the disclosure and aiding in the understanding of one or more of the various aspects of the presently described systems and methods. This method of disclosure, however, is not to be interpreted as reflecting an intention that certain embodiments require more features than are expressly recited in each claim. Rather, as the following claims reflect, certain aspects of the disclosed systems and methods may lie in less than all features of a single foregoing disclosed embodiment. Thus, the claims following the detailed description are hereby expressly incorporated into this detailed description, with each claim standing on its own as a separate embodiment of the present disclosure.

Furthermore, while some embodiments described herein include some but not other features included in other embodiments, combinations of features of different embodiments are meant to be within the scope of the present disclosure, and form different embodiments, as would be understood by those in the art. For example, in the following claims, any of the claimed embodiments can be used in any combination.

In the description provided herein, numerous specific details are set forth. However, it is understood that embodiments of the present disclosure may be practiced without these specific details. In other instances, well-known methods, structures and techniques have not been shown in detail in order not to obscure an understanding of this description.

Where in embodiments of the present disclosure reference is made to "nucleic acid carrier," reference is made to any cell, membrane, or body containing nucleic acid. For example, a nucleic acid carrier may be a cell, a eukaryotic cell or the nucleus thereof, a bacteria, a virus, etc.

Where in embodiments of the present disclosure reference is made to "micropillar," reference is made to a microstructure obtained on a substrate. The pillars are typically cylindrical, but may have other shapes such as prismatic or pyramidal, and may have any suitable top cross section, such as circular, rhomboid, square, etc. A set of micropillars typically may be referred to as a micropillar array. Micropillars in an array are preferably organized following a predetermined pattern, although a random pattern also may be used.

The present disclosure relates to on-chip reactors for nucleic acid amplification, in which a predetermined portion of a nucleic acid molecule can be identified and detected (e.g., by replicating the portion over a detection threshold and making it detectable, e.g., by staining). Typically, polymerase chain reaction (PCR) is used, which is a multi-step chemical reaction in which nucleic acid and other reagents and compositions participate (e.g., two primers, polymerase, nucleotides, etc.), usually taking place under controlled thermal conditions, because temperatures over 90° C. and controlled timing is required. Nevertheless, embodiments are not limited thereto and for example isothermal amplification reactions also are encompassed by embodiments of the present disclosure.

In procedures comprising nucleic acid extraction and/or purification, nucleic acid needs to be extracted from carriers containing it (bacteria, cells, nucleus, virus, etc.). Further, the carriers are usually immersed in a complex matrix, such as blood, bodily fluids, organic matter, etc., which makes isolation of nucleic acid more difficult. Extraction and/or purification of nucleic acid is usually done by breaking the membrane or wall of the carrier (lysis) and separating debris (proteins, lipids, etc.) from the nucleic acid. For purification, several techniques can be used, such as sequential washing with buffers. Common off-chip techniques include sequential filtering, washing and an elution step. Alternatively, binding of particles, washing and separating the nucleic acid can be done, in which filters and/or magnetic silica beads are added after lysis and washed, before magnetically separating the nucleic acid from the rest of particles. Finally, elution is performed, after which the purified nucleic acid can be introduced in the PCR reactor. Nucleic acids of an entire sample are used as a template for PCR. The method may include other steps such as centrifugation or solubilization, dilution, etc., depending on the particular application.

On-chip procedures provide nucleic acid extraction and purification on microfluidics platforms. These chips usually comprise a substrate with microfluidic channels (and optionally valves, mixers, reservoirs, inlets, outlets, etc.) and a protective lid. For example, fluid is introduced in the chip through a window, e.g., on the lid, via a microfluidic channel into a cavity containing a separation column, which acts as filter and purifier. Reagents are also introduced in the chip and mixed with the sample to be tested. The separation column may be a micropillar array for filtration. After the nucleic acid is extracted and optionally purified, it can be sent via microfluidic channels to a thermally insulated PCR cavity.

In a first aspect, the present disclosure provides a microfluidics system adapted for analyzing a fluid sample. The system comprises a substrate comprising at least one cavity, and means for introducing a fluid sample in the cavity. The at least one cavity further comprising a surface adapted to provide nucleic acid extraction and/or purification. The system also comprises a controller for inducing in the cavity nucleic acid extraction and/or purification conditions for inducing nucleic acid extraction and/or purification in the cavity and subsequently inducing nucleic acid amplification conditions for inducing nucleic acid amplification in the same cavity. In some embodiments, extraction and purification and amplification is performed in one and the same cavity. Thus, there is no need to send the nucleic acid to a different part of the chip, or to a different chip, for PCR. The setup can be made very compact.

Hence, the present disclosure allows introducing the nucleic acid carriers (virus, bacteria, cells) directly into the device. This saves time, because there is no need to extract the carrier first and then send it to a further reaction cavity. Additionally, the procedure is systematic and it removes human influence and errors in nucleic acid extraction and purification for the same type of samples. In some embodiments of the present disclosure, all the steps of nucleic acid extraction and purification are performed in the polymerase chain reaction cavity.

By way of illustration the corresponding processes as conventionally done and as done in embodiments according to the present disclosure are compared below. In conventional methods, typically two processes are performed, i.e., standard nucleic acid extraction on the one hand and standard nucleic acid amplification on the other hand. In the standard nucleic acid extraction process, typically the following steps are performed: first there is sample lysis, followed by a mix with binding buffers, followed by nucleic acid binding. Thereafter, washing steps are performed and afterwards nucleic acid elution. In a subsequent process, PCR reagents are added to the eluate, heat cycling is performed and thereafter a detection is done. In contrast, in embodiments of the present disclosure, wherein nucleic acid extraction and amplification are performed in a single chamber, there is no elution. The process comprises the steps of sample lysis, mixing with a binding buffer, nucleic acid binding, washing steps, addition of PCR reagents, performing heat cycling, and a detection step. In some embodiments, the elution step can be omitted.

Further features and advantages will be discussed with reference to the drawings illustrating exemplary systems with standard and optional features.

FIG. 1 shows a device for PCR and nucleic acid extraction and/or purification implemented in a substrate 101. More generally, the platform of embodiments of the present disclosure may comprise a chip (for example, a Lab-on-a-Chip system) including a substrate that can withstand the conditions for PCR (e.g., high temperatures). The chip may also be compatible with other microfluidic systems. In some embodiments, the substrate comprises semiconductors, such as silicon, whose production and processing routes are well-known and reliable in electronics and microfluidics. Silicon is widely available, easily integrable with electronics, inexpensive, and the production, manufacture, and processing routes are well-known. For example, a cavity and microfluidic channels can be reliably provided by several techniques (etching, reactive ion etching, etc.). However, the present disclosure is not limited to silicon substrates, and the substrate may comprise, for example, glass, ceramics, or oxides, other semiconductors, polymers, or a mixture thereof.

The chip can be covered by a sheet or lid (comprising, e.g., ceramic, plastic, polymeric, and/or semiconducting materials), in order to protect and isolate the fluids. The lid may present hydrophobic properties, for keeping the fluids confined to the cavity. The lid can be transparent, or transparent only in predetermined areas, for optical inspection of the fluids. The lid can be bonded to the substrate (e.g., anodic bonding, or by sealing means such as glue, epoxy, etc. In some embodiments of the present disclosure, the chip and/or lid may comprise windows or openings (e.g., backside openings, etc.) serving as inlets of reagents and samples, and outlets for removing waste or reacted material from the system, or for transferring the reacted material to an analysis unit. Some or all windows may be sealable, for example for control of pressure or for avoiding disturbing the reaction.

In the example shown in FIG. 1, the substrate 101 comprises a plurality of fluid reservoirs 102, 103, e.g., a reservoir for receiving a sample containing genetic material (such as a fluid with virus or white blood cells), and a reservoir for receiving reagents and or buffers. In FIG. 1, a set of microfluidic channels 104, 105, 106 for directing and mixing the fluids is provided. In some embodiments of the present disclosure, the substrate thus comprises microfluidic channels and mixers, for example a meandering portion of the channel for mixing reagents and/or buffer, for example binding buffer, with sample, before introducing the mixture in the extraction and/or purification/PCR cavity. The mixer (e.g., a mixing channel) may comprise a T-junction, a meandering microfluidic channel, or any other mixing means.

In some embodiments, the surfaces of the substrate comprise hydrophilic properties for improving filling of the microfluidic channels and cavity. In some embodiments, the surface can also present antifouling properties, which can reduce deposits and contamination.

A cavity 107 in the substrate serves as a reaction cavity for PCR. The cavity for extraction and/or purification and PCR may have a size varying in the 1-10 mm range and volumes from fL to 10's of μL. In some embodiments, a typical diameter of the cavity may be restricted to 10 μm or smaller (tenth of picoliter volume); in this way the diffusion time needed for the nucleic acid fragments to reach the surface is limited. If cavities are very small, no pillars are needed to reduce diffusion times. If cavities are larger, pillars can be introduced to limit the diffusion length and to increase the surface area. The cavity of the present disclosure includes means for providing lysis and nucleic acid extraction and/or purification. Such means may include, but are not limited to, micropillar filters. In FIG. 1 an array of micropillars 108 is shown on the surface of the cavity.

The array serves as a nucleic extraction and/or purification unit. It also serves as a capillary pump.

In some embodiments, the cavity comprises a silicon-based pillar filter. The silicon-based pillar filter may comprise a plurality of micropillar structures. Micropillars provide an increased area of the surface. This is advantageous for example in binding, because more nucleic acid can be attached to the surface during extraction and/or purification. The cavity is provided in the platform, e.g., on the substrate. Micropillar filters may have any suitable configuration or shape. For example, they may form a regular array of pillars, e.g., cylindrical pillars with a diameter of 15 microns and interpillar spacing of 25 microns and height of 300 μm. They may be obtained on a silicon substrate, e.g., by etching, reactive ion etching (ME), deep ME, etc. The characteristics of the etching process link together and set a limit to interpillar distance and pillar height. E.g., if a DRIE process is used, the aspect ratio of the etch can be stretched to 50, 30 being a more relaxed value; hence for a pillar height of 300 µm, e.g., between 150 µm and 50 µm, e.g., between 30 µm and 1 µm interpillar distances of 10 µm or smaller, e.g., 5 µm or smaller, e.g., 2 µm or smaller can be achieved.

Figure 16:
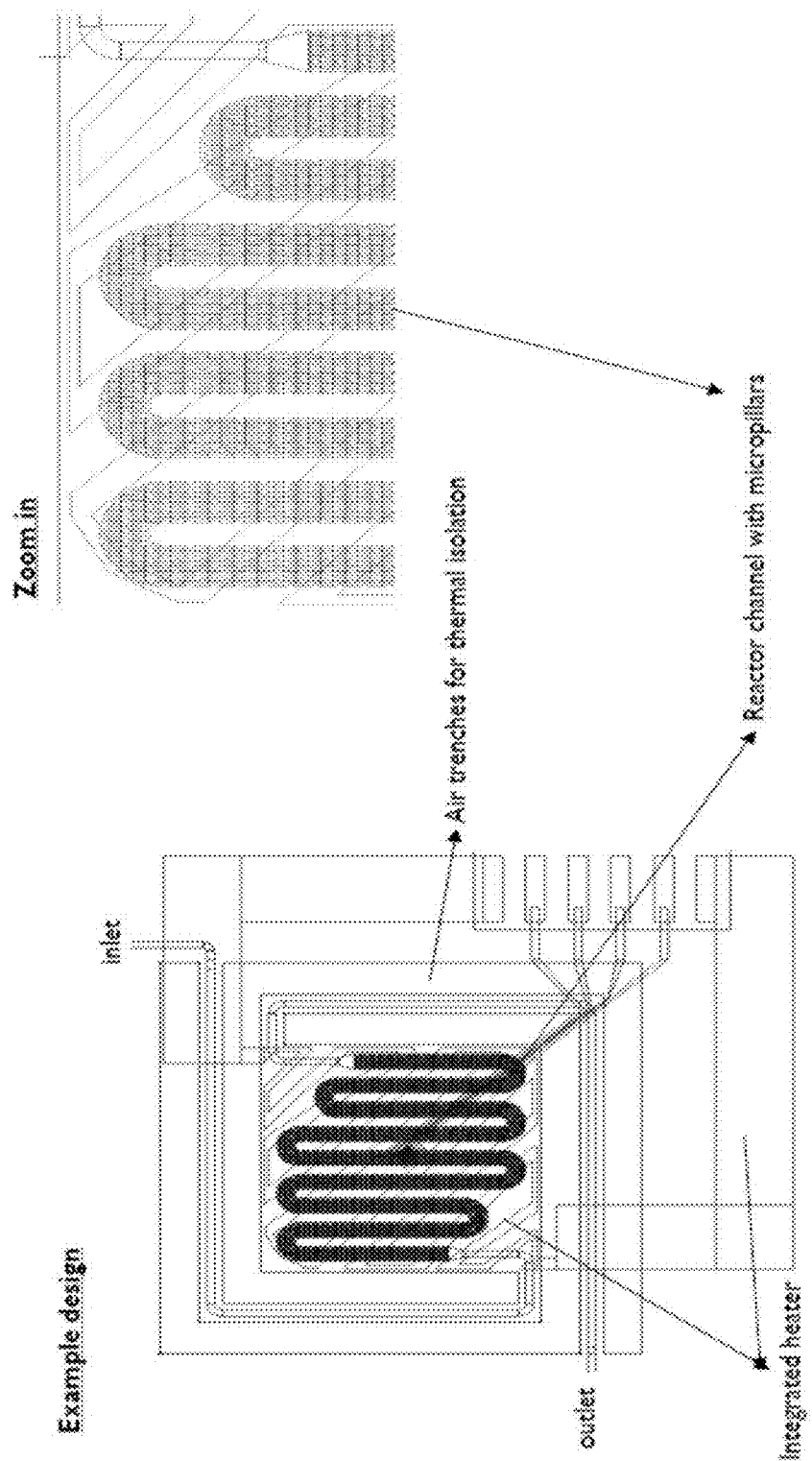
FIG. 16 shows a design for a chip for combined extraction and PCR, according to an example embodiment of the present disclosure.
Figure 17:
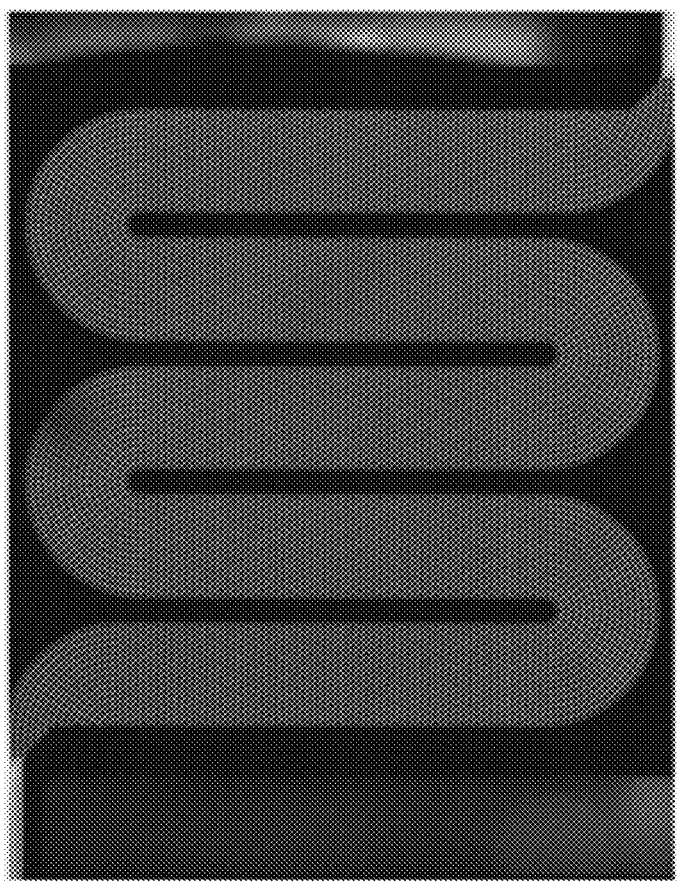
FIG. 17 shows a fluorescent picture of a chip after combining extraction and PCR, illustrating features of example embodiments of the present disclosure.

By way of illustration, embodiments of the present disclosure not being limited thereto, a possible example design for a chip for combined extraction and PCR is shown in FIG. 16. The chip shows an inlet (also referred to as input), an outlet, an integrated heater, and a microfluidic reactor channel with micropillars. It also indicates a thermal isolation, in the present example being air trenches. In the drawing, a zoomed-in area is shown. FIG. 17 illustrates a fluorescent picture of a microfluidic channel of a chip after combined extraction and PCR. The pillars can be clearly seen.

The cavity 107 further comprises means to provide temperature control. In some embodiments of the present disclosure, the substrate comprises heater (e.g., resistor) and sensors (e.g., a resistive thermometer). A temperature controller may optionally be externally provided, e.g., connected to the heaters and/or temperature sensors via, e.g., bondpads, or may be integrated in the platform. In embodiments of the present disclosure, an external unit may heat up the fluid in the cavity. In some embodiments, heaters may surround the cavity, or may be comprised under the cavity. A dedicated heater in the cavity improves temperature control of the fluid. Heaters may be integrated in the substrate, for example on a surface of the substrate, for example the surface opposite to the surface wherein the cavity is provided, e.g., back-side heaters. In further embodiments, heaters may be provided in the lid of the platform. The heaters may be strips of resistive material, or small plates, which heats up upon application of a controlled current. The integrated heater and trenches can be made very compact. In embodiments of the present disclosure, the system comprises means to provide thermal isolation to the cavity or cavities.

Thermal isolation is provided in this example by surrounding trenches 109, and a heater 110 is included, e.g., under the reaction cavity, but this example is not limiting and heating means may also be at the sides, between the cavity walls and the trench. In some embodiments, trenches only partially surround the cavity, for example, half of it. They can also surround the whole cavity except for the microfluidic channels.

Further, the reaction cavity may include an outlet 111 for removing waste material. Additionally, the outlet 111 may provide pumping via, e.g., suction. Other features may be included, such as a valve in the intersection between the channels 104, 105 connecting the reservoirs 102, 103, and the mixer 106, etc.

The nucleic acid extraction and/or purification process may be performed in any suitable way. For example, the cavity may comprise means for solid state separation, such as the Boom method, which comprises binding of nucleic acid on a surface, washing away debris such as lipids or proteins, and eluting the nucleic acid, detaching it from the surfaces before performing PCR in the same cavity. For instance, the cavity may comprise an area coated with silica particles which act as beads, which are widely available. Additionally or alternatively, the cavity may comprise a flat surface, for example a Si-comprising surface such as silicon oxide, although other oxides or dielectrics also could be used, such as for example $TiO_x$, $TaO_x$, $SiN_x$, etc. The micropillars themselves may comprise surfaces which can be used for solid state separation. For example, the micropillars may be coated, and/or an oxide deposition can be performed.

In some embodiments, the system also comprises a controller, not shown in FIG. 1, for controlling the nucleic extraction and/or purification step by providing the proper conditions for performing nucleic extraction and/or purification, e.g., providing the appropriate buffer material and/or providing the appropriate environmental conditions, such as temperature, pH, etc. The controller may be connected to a plurality of valves for controlling the inlet of the sample, the reagents and the buffer materials and may be connected to a driving unit of the heater for controlling temperature. It may also be connected to feedback elements for obtaining feedback regarding the conditions. It may comprise a timing means for controlling the length of the extraction and/or purification step as well of the step of nucleic amplification, for which the controller has induced the proper conditions, subsequently to the extraction and/or purification step.

Figure 2:
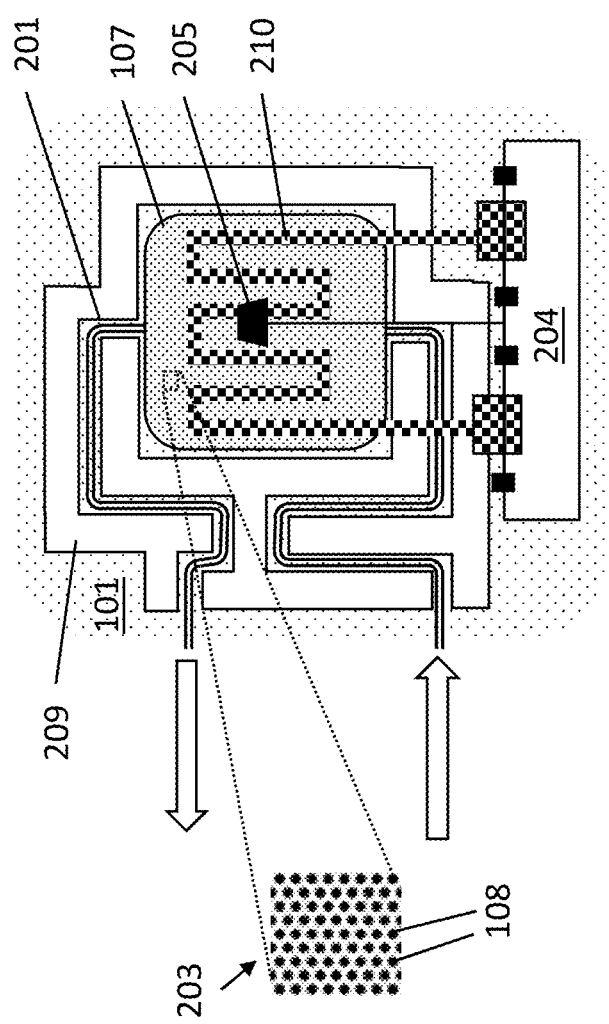
FIG. 2 illustrates a platform according to example embodiments of the present disclosure, showing connections for a heater and sensors.

FIG. 2 shows a more detailed example embodiment in which a particular trench 209 surrounds part of the microfluidic channels included in parts 201 of the substrate. The length of the channels is also purposely increased inside the trench area. This contributes in the reduction of the influence of temperature in other parts of the platform. The arrows indicate the direction of fluids into and outside the cavity 107. As before, the cavity comprises an array 203 of micropillars 108 for providing nucleic acid extraction and/or purification. The particular heater 210 comprises a resistive strip comprising connections 204 (e.g., a bondpad) for external connection to a power source and/or controller. Additionally, a temperature sensor 205 is included for obtaining readouts of the temperature in the cavity (e.g., via connections to external reading units, e.g., via bondpads), allowing accurate control of the PCR process. It is to be noted that, in this example, the heater is shown integrated into the lid. Alternatively, if the heater is integrated on the backside or front side of the silicon it typically does not cross the trenches and should follow the same path as the channels.

In some embodiments, the introduction of reagents and sample can be done under controlled pressure. For example, the reagent reservoir is filled while the sample and outlet, used as vent which can be used to control the pressure of the cavity, are sealed. The reagent reservoir would fill the channels until the pressure does not allow further filling. The sample inlet or reservoir is unsealed, allowing further filling of the channels, and a fluid sample is placed on the reservoir. After unsealing the outlet, the mixing process starts, and finally the reaction chamber (which may act in the same time as capillary pump) is filled with the sample and reagent mixture.

Figure 3:
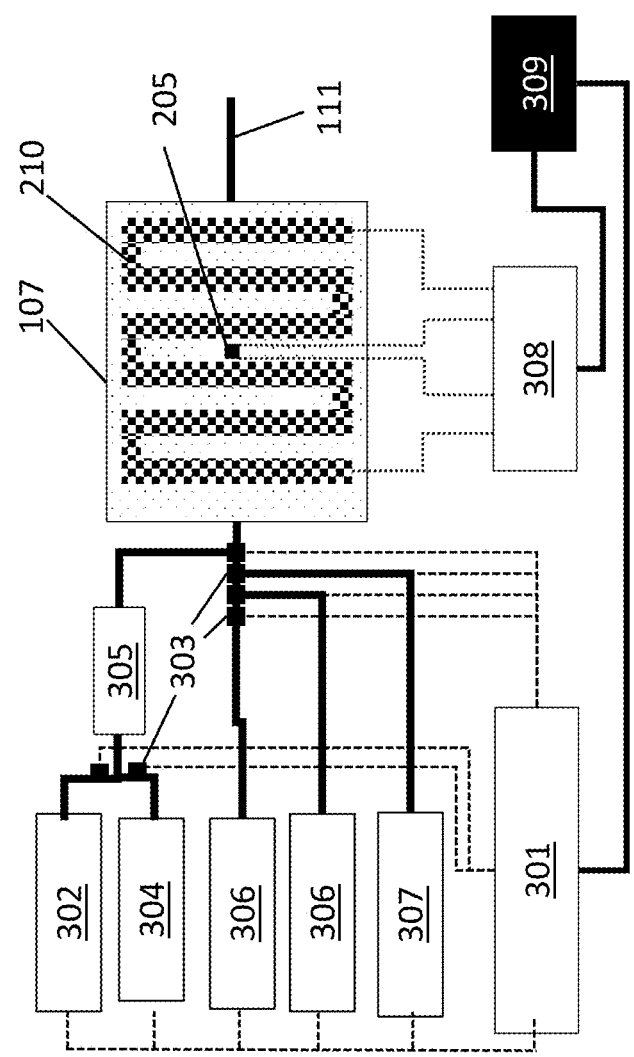
FIG. 3 illustrates a pressure and valve system for control of fluids in a microfluidics platform according to example embodiments of the present disclosure.

In some embodiments, the filling is active and dynamic control of valves is used for introduction of reagents, sample, buffers, etc., as shown in FIG. 2 and FIG. 3. The valves may comprise capillary valves with electrical actuation, trigger valves actuated by the fluid, etc.

FIG. 3 shows an example embodiment of a system based on pressure-driven operation. A fluidic controller 301 controls pumps 302 (e.g., syringe pumps) and valves 303. In such an embodiment, sample and binding buffer are introduced in the microfluidic channels via respective pumps 302, 304 and the fluids are sent to a mixer 305 (e.g., a T-mixer, mixing channels, etc.) before introducing the wash buffers and the reagents. In this case, two further pumps 306 introduce two wash buffers (which may be the same or different) and a fifth pump 307 for the PCR reagents, respectively, in the microfluidic channel. The fluids are mixed with the sample and binding buffer together in the channels and pumped into the cavity 107 for nucleic acid extraction and/or purification. Extraction and/or purification may comprise for example thermal lysis or by chemical or enzymatic lysis induced by temperature, and then binding on the surface of the cavity and purifying the nucleic acid, followed by PCR. A heater 210 and thermometer 205 are used to control the temperature of the process, using a temperature controller 308. A central processing unit 309 (e.g., a processor, computer, etc) can be used to monitor and control the temperature and fluidic controllers. Thus, the procedure can be automatic—the sequential introduction of sample, binders, buffers and reagents can be programmed to ensure complete extraction and/or purification, drying and elution, as well as programming one or more PCR cycles.

In some embodiments of the present disclosure, capillary pumping can be provided by a capillary pump, for example, induced by an array of micropillars placed in a further cavity. In some embodiments of the present disclosure, the arrangement of micropillars in the reaction cavity can additionally also be used as pump.

Figure 4:
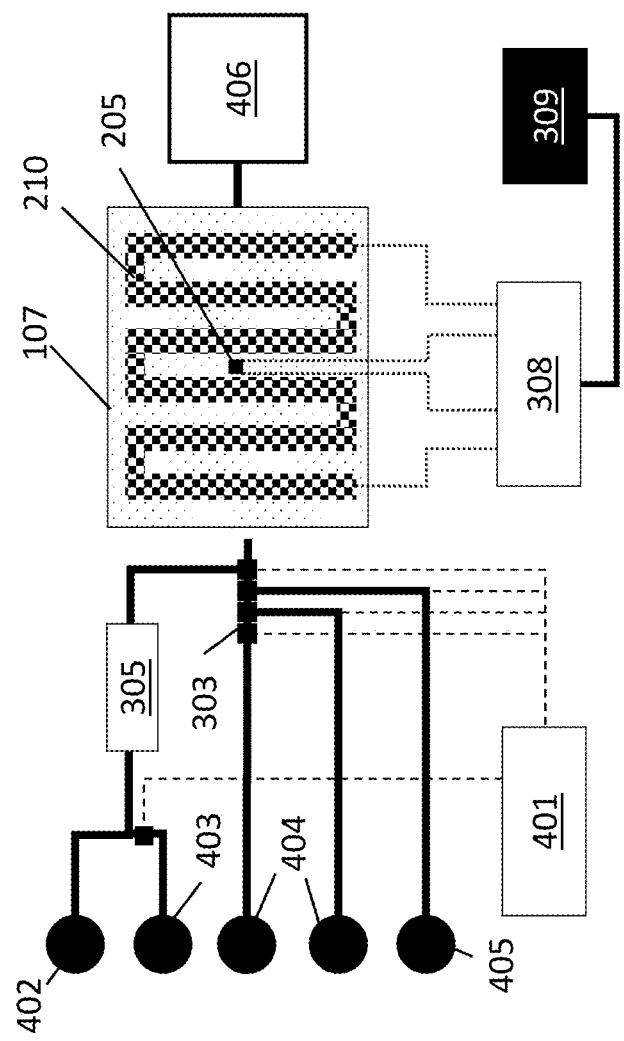
FIG. 4 illustrates an alternative valve system with capillary pumping according to example embodiments of the present disclosure.

FIG. 4 shows another example embodiment of a system based on capillary-driven operation. A valve controller 401 controls the introduction of fluids in the system. The fluid control in this case is done only by valves, not via valves and pumps as in FIG. 3. In this example embodiment, sample and binding buffer are introduced in the microfluidic channels through reservoirs 402, 403 which may be filled by pipetting on an opening in the lid or substrate. The fluids are sent to a mixer 305 before introducing the wash buffers and the PRC reagents via their respective reservoirs 404, 405. The fluids are dragged inside the PCR cavity 107 under the pulling pressure of the capillary pump 406. In the present example, the temperature controller 308 controls and monitors the heater 210 and thermometer 205. It has, in the present example, a central processing unit 309 (e.g., a processor, computer, etc.) that can be used to monitor and control the temperature controller and optionally a separate valve controller. In other words, the controller can be either centralized fulfilling all tasks centrally or can be, as shown in the present example, de-centralized whereby different functions are performed in different sub-controllers.

By way of illustration, nucleic acid extraction using a cavity with silicon-based micropillars is schematically shown in FIG. 19, wherein in the upper drawing the pillar structure is shown, wherein the middle drawing shows the elution process, illustrating the sample input, the nucleic acid binding, washing steps and an elution step, and wherein the lower graph illustrates the effect of extraction by showing the amount of DNA that can be recovered as function of the amount of applied DNA.

Figure 18:
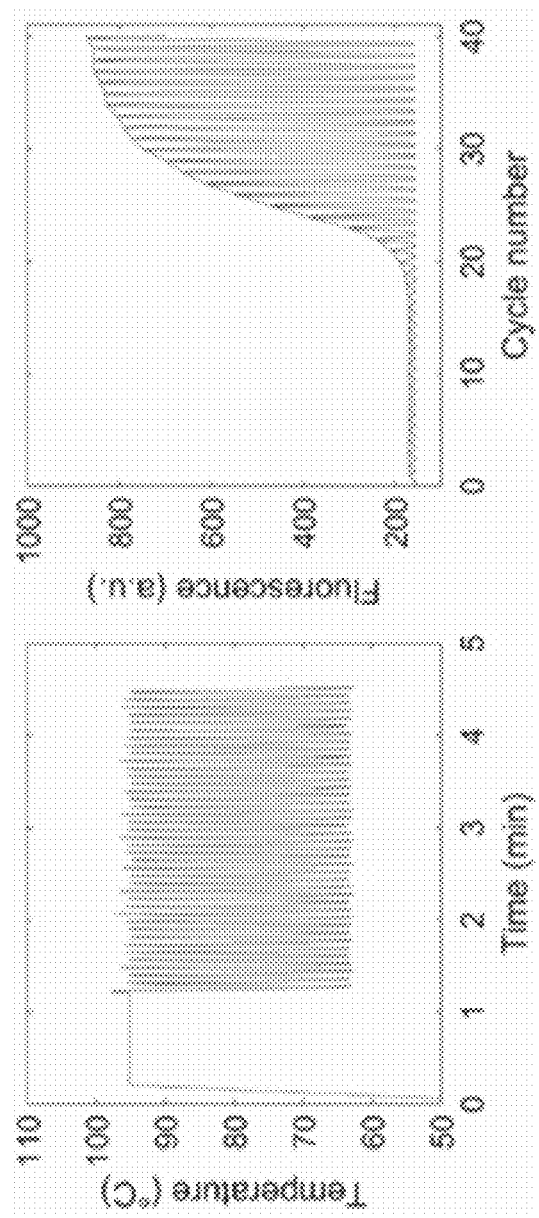
FIG. 18 shows the applied temperature process and the resulting fluorescence signal upon PCR on-chip detection in silicon microchips, illustrating features of example embodiments of the present disclosure.

The fact that PCR itself can be obtained using silicon chips has been illustrated by Cai Q. et al. in Talanta 2019 (192) pp. 220-225 and by Powell L. et al. in Analyst 2018 (143(11)) pp. 2596-2603. The temperature variation used during the PCR process as well as the fluorescence signal resulting from the PCR process is shown in FIG. 18.

According to some embodiments, the washing steps applied may be at a lower flow rate than for conventional processes where elution is performed, in order to avoid washing away nucleic acids from the single cavity. Furthermore, in some embodiments, heating cycles may be applied in addition to or different from heating cycles in conventional processes where elution is performed, in order to compensate for nucleic acid gradients occurring over the cavity due to the flow that are being present.

In a second aspect of the present disclosure, a system for PCR is provided, which is advantageous for multiplexing detection measurements. While traditional quantitative PCR can be used to detect several targets (because a bundle of reagents can be used), competition and other effects usually take place, which does not enable good multiplexing. On the other hand, in PCR according to embodiments of the present disclosure, competition is less problematic. PCR that can be performed that is, for example, digital PCR or qPCR. Digital PCR has the benefit over other techniques such as real time PCR (qPCR), in that it does not require calibration standards and gives a direct, absolute concentration.

In embodiments of the second aspect of the present disclosure, a plurality of cavities (or partitions, in the frame of PCR) according to embodiments of the first aspect are preferably provided in a single substrate such as silicon or polymer, or polymer on top of silicon, but they may be provided in different substrates. In particular, the partitions may comprise hydrophilic surfaces with antifouling properties. For vertical integration, the top may advantageously be made hydrophobic. A single fluidic sample may be partitioned between the cavities in the system. In embodiments of the present disclosure of dPCR, the sample can be diluted such that a well (e.g., a microarray of micro-cavities) only contains, on average, less than one, one or only a few template copies, and it provides a way to obtain absolute nucleic acid levels directly using end point analysis (which are able to characterize the presence of PCR products after the end of the reaction), with high resolution and sensitivity. In some embodiments, the fluidic sample may comprise cells or other nucleic acid carriers, and there is no need to perform a pre-extraction before introducing the sample in the reaction cavities for dPCR.

In dPCR, the samples are prepared to ensure the array comprises a number of partitions higher than the number of nucleic acid carriers (e.g., by providing a predetermined concentration of sample, taking into account that the number of targets should be lower than the number of cavities in the array), for obtaining an average of less than a nucleic acid carrier per partition. In some embodiments of the present disclosure, the partition number can be between 496 to thousands or even millions, for example 10 million partitions; for example, embodiments of the present disclosure may comprise 10000 partitions or more. In some embodiments, each cavity of the array may have a capacity of 1 fL to 50 nL, for example, a capacity of 100 pL. This increases the chances that a cavity will contain a small number of nucleic acid carriers.

The digital array can be integrated vertically, providing the fluid on top of the cavities, for example, through vias (e.g., Si vias). This is shown in the leftmost drawing 500 of FIG. 5, in which an inlet 501 serves to introduce and distribute the fluids in a platform containing the array 502 of cavities 507, which can be later removed towards an outlet 503 through the vias 504 (which can be, for example, silicon vias obtained according to well-known silicon processing routes). In further embodiments, the network of cavities 511 are filled through channels 512. In a central drawing 510 of FIG. 5, fluid is sent to the cavities from a first channel 512. In the cavities, lysis (e.g., thermal lysis), binding and washing can be performed, and the excess fluid can be removed via a further channel 513 before PCR. If needed, for example, before PCR, a second fluid 521 (such as oil) can be introduced to through channels in order to fluidically isolate the cavities of the array 511. In some embodiments, multiple layers are used, e.g., by combination of the vertical and horizontal configurations 500, 510.

In some embodiments of the present disclosure, thermal insulation (e.g., a trench) is provided around each microcavity or around a plurality thereof. Similarly, a heater may be provided to heat up each cavity or a plurality thereof. This gives a great control over the PCR in the array. In some embodiments, a group of cavities from the array (e.g., a subset) may be heated up by the same heating element, which may be overlapping the cavities, in the backside of the substrate or on the lid. For example, a single heating element may be arranged with respect to the cavities such that their contents can all be simultaneously and efficiently heated up. For example, a single meandering resistor, or a single plate overlapping the array, may heat up all the microcavities.

By way of illustration, an exemplary workflow for performing digital extraction in an array of cavities for combined extraction and amplification is described below. The process comprises dividing the sample over the array, performing sample lysis in a binding buffer, performing nucleic acid binding, performing one or more washing steps, adding PCR reagents, performing a heat cycling, and a detection step. Compared to the combination of the standard nucleic acid extraction and nucleic acid amplification steps, again, no elution is performed.

Figure 6:
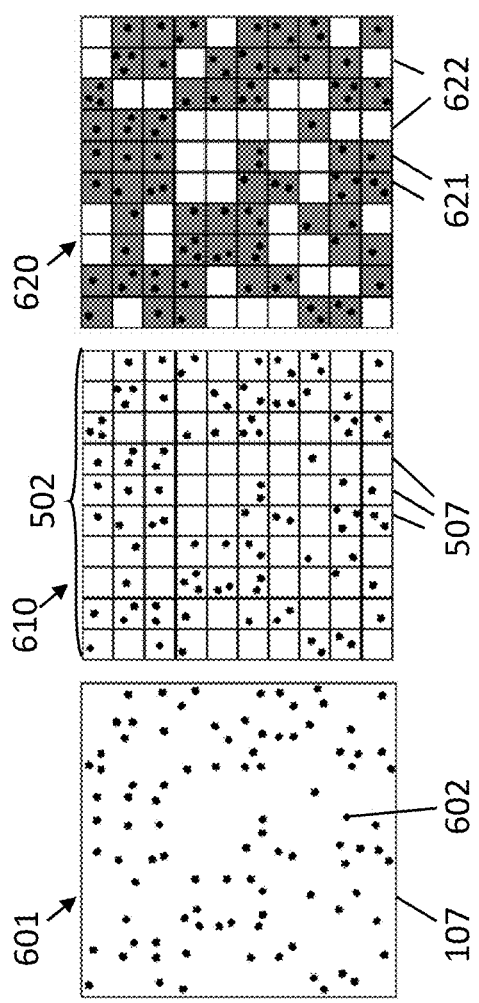
FIG. 6 illustrates a comparison between PCR in a single cavity and PCR in multiple cavities.

FIG. 6 shows an exemplary comparison between a PCR in a single cavity versus a dPCR in an array of cavities. In the leftmost drawing 601, a single cavity 107 with many positive targets 602 is shown. When applying PCR on this large cavity, the PCR will give a positive result (the target nucleic acid, or portion thereof, is present in the sample). However, the exact concentration is not known. In the middle drawing 610, the sample is partitioned and distributed in a cavity array 502 (comprising, e.g., one hundred cavities 507 in this example). In this example, 61 cavities contain at least one copy (dark cavities 621 in the rightmost drawing 620), while the other 39 cavities are empty (blank cavities 622 in the rightmost drawing 620), which remain negative after amplification. The ratio of positive versus negative cavities depends on the initial target concentration, which can be calculated using Poisson statistics. In this example, the average concentration was taken as 1 which, theoretically should result in 63 positive cavities. Increasing the number of cavities (thus lowering the average expected number of targets per well) results in higher accuracy of the measurement.

The dPCR setup is advantageous in cases where there are few copies of a gene target compared to a competitive fragment. For example, this may happen if there is too little fetal DNA and too much maternal background. Basically, the same effects of dPCR can be obtained, but directly on complex matrices such as blood, soil, feces, etc. It is possible to detect and quantify small percent copy number differences with a high degree of precision. In mutation analysis, it is possible to detect and quantify rare mutations for low-prevalence targets (for cancer research samples). Also, for low level pathogen detection and viral load quantification, it is possible to obtain absolute quantification and pathogen counts, as well as to detect low-level pathogens that cause human illnesses (e.g., through contaminated food and water supplies). This technique could generate absolute reference standards for genetic measurements, metrology and cross-lab comparisons, because the critical process of DNA extraction and/or purification is not influenced by human factors. It can also be used for agricultural and farming purposes, by allowing sensitive detection and absolute quantification of plant mutations and genetically modified organisms.

Multiplex dPCR techniques originating from the same nucleic acid carrier can also be applied within embodiments of the present disclosure. For example, multiplexing of a single type of nucleic acid carrier (a virus, a type of bacterium, a type of cell) can be done. Within this framework, it is possible to analyze combined presence of genetic markers, such as those linked to antibiotic resistance to bacterial species, or analyzing whether two mutations appear together, etc., as well as co-expression of specific genes.

According to embodiments of the present disclosure, studies on differential gene expression (including detection of gene expression changes between single cells, or linking expression level of predetermined markers, e.g., mRNA, to single cell/entity) are possible, as well as single-cell variant calling, which may help decreasing false positive and negative calling by studying the genetic make-up on single cells. It is also possible to introduce PCR adapters on single-cell level using whole-genome amplification techniques for sample preparation, as part of next-generation sequencing. The present disclosure is not limited to these applications, and it can, for example, also be used for studying single cell epigenetic markers.

It is to be noticed that in one aspect, the PCR does not need to be performed in a cavity wherein both the extraction and/or purification as well as the amplification is performed. Whereas this is a characteristic of embodiments of the first aspect, in embodiments of the second aspect this can be done in separate cavities, but possibly on the same substrate. In other words, in embodiments of the second aspect, the extraction and/or purification does not need to be performed in the same cavities as where the amplification is performed.

Figure 7:
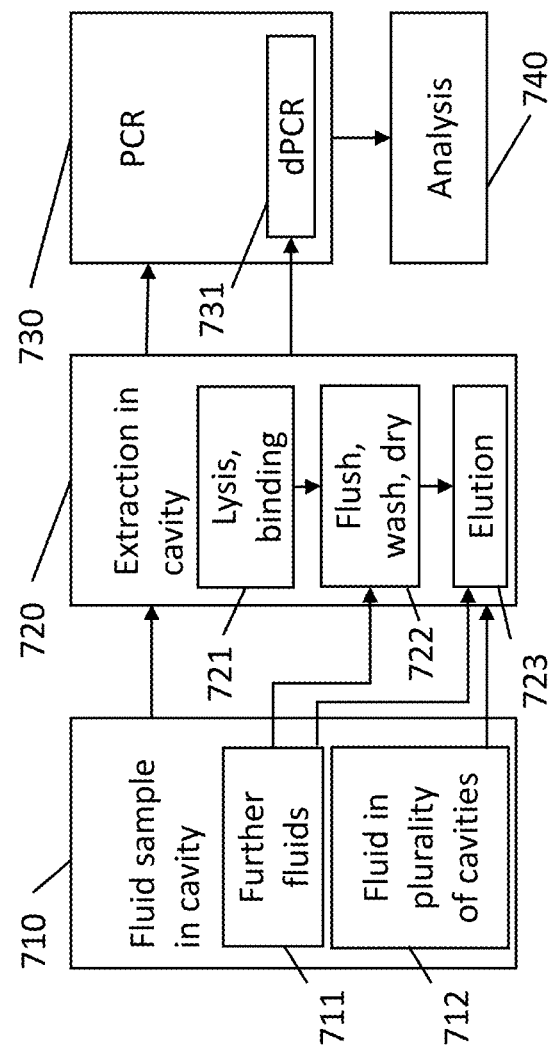
FIG. 7 shows a flowchart of a PCR method according to example embodiments of the present disclosure.

In a third aspect, the disclosure provides a method for obtaining nucleic acid amplification. In embodiments of the third aspect of the present disclosure, PCR can be provided, including techniques based on PCR such as qPCR and dPCR. The general method is outlined in the flowchart of FIG. 7. The method comprises the steps of providing 710 fluid (a sample containing nucleic acid carriers, optionally mixed with binding buffers, reagents, etc.) in at least one cavity adapted to provide nucleic acid extraction and/or purification (e.g., comprising a micropillar array). The introduction and mixing, as well as introducing any further wash buffer and/or reagent 711, can be made via microfluidic channels. The method may comprise also introducing fluid 712 in a plurality of cavities for PCR. This step may comprise directly providing harvested cells, as no pre-extraction is required.

The method further comprises extracting or purifying 720 nucleic acid in the cavity, for example by solid phase extraction and/or purification. For instance, the method may comprise providing 721 lysis and binding to a surface, for example to a coated surface, which may be on the surface of the cavity, e.g., on the micropillars. Lysis can for example be thermal lysis or by chemical or enzymatic lysis, which may be induced by temperature. Binding can be done by a pre-mixture of the sample with a binding buffer adapted to enhance binding to a surface, for example silica particles, silicon oxide wafers, or the surface of pillars. Pillars may be introduced for reducing the diffusion time (to ensure nucleic acids have a surface to bind during the assay) and to increase the surface area (to ensure there is enough surface for all nucleic acids to bind). The pillars also may assist to keep the nucleic acid containers in place and to help for capillary flow actuation. A step providing 722 flushing, washing (for removing debris, leaving the bound nucleic acid) and drying in the cavity or cavity array can be performed, followed by providing 723 elution, for example with a PCR buffer. These steps of providing 722 flushing and providing 723 elution can be performed by sequentially introducing 711 these further fluids in the cavity or cavity array.

The method further comprises providing 730 nucleic acid amplification in the same cavity via PCR, or optionally providing 731 amplification in a cavity array, thereby obtaining dPCR. This step may comprise sub-steps, such as heating and annealing the cavity or cavity array, etc.

Finally, the method may optionally comprise performing 740 analysis, e.g., detecting increased fluorescence (from intercalating DNA dyes, fluorophore-labelled probes or oligonucleotides, etc.), or by any other technique known in the art, in the same cavity or cavities of the array.

In one aspect, embodiments thus also relate to a method for analyzing a fluid sample, the method comprising obtaining a diluted fluid sample in a plurality of cavities of a substrate, introducing buffers and/or reagents, performing nucleic acid extraction and/or purification, performing nucleic acid amplification, and the plurality of cavities for determining a concentration of a target in the fluid sample. As indicated above, the extraction and/or purification may be performed in the same cavities as the amplification, although in one aspect the methods are not limited thereto and can be performed in different cavities, e.g., cavities on the substrate.

EXAMPLES

Figure 8:
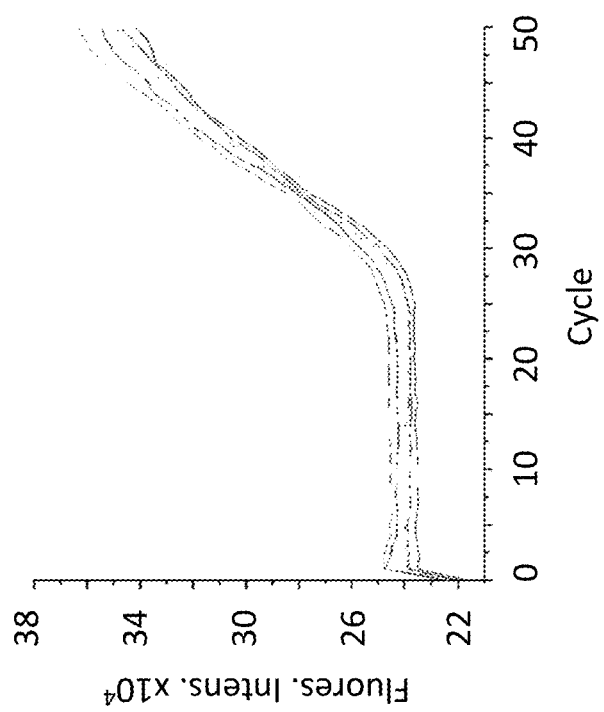
FIG. 8 illustrates a graph showing the fluorescence intensity as a function of the number of cycles of a sample studied according to example embodiments of the present disclosure.

In order to perform PCR, a standard PCR protocol was performed using a single cavity comprising micropillars and front side heaters. As an example, standard PCR was used. More specifically, a PCR master mix (2×dPCR Master Mix for Probes, BioRad, 186-3010) mixed with primers (BioRad dPCR EGFR, FAM probe) and human DNA as a template. A standard amplification protocol was used, namely enzyme activation for 5 minutes at 95° C. followed by 50 cycles of 15 s at 95° C. and 45 s at 60° C. As shown in FIG. 8, a noticeable typical amplification curve with an increase in fluorescence per amplification cycle can be observed signifying successful DNA amplification.

Figure 9:
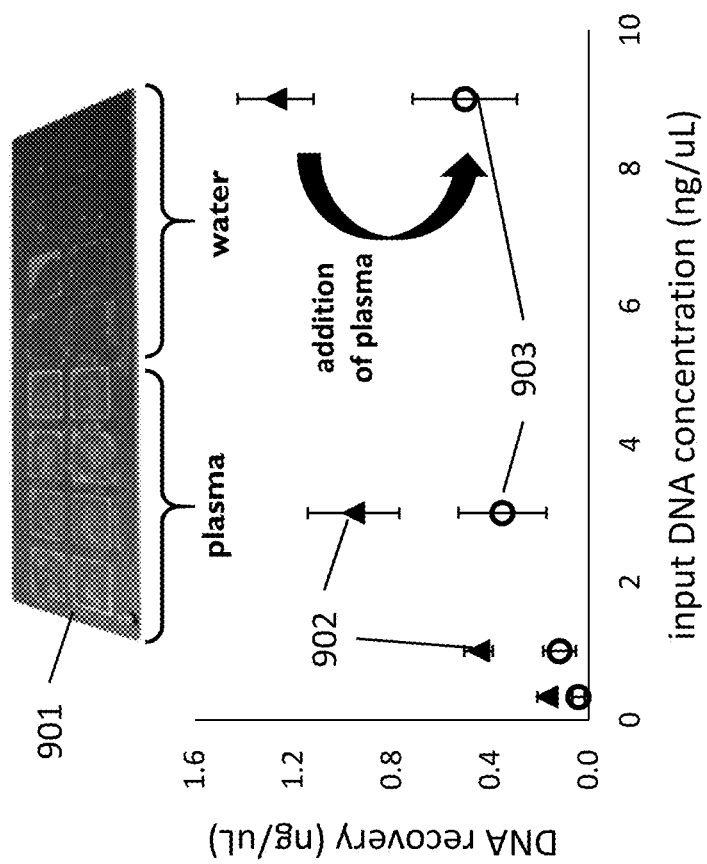
FIG. 9 illustrates the DNA recoveries of a DNA in water and in plasma for a surface comprising a silicon wafer according to example embodiments of the present disclosure.

Different DNA recoveries have been observed for samples after DNA extraction and/or purification on a cavity comprising a silicon oxide surface (a wafer 901), as shown in FIG. 9 for water (triangular graph points 902) and for plasma (circles 903). A significant decrease in DNA recovery is observed for all DNA concentrations after addition of plasma. A clear debris stain was observed for all DNA samples where plasma was present. This indicates a reduced DNA binding capacity, but even this reduced capacity should be sufficient for most applications. Alternatively, extra pillars can be introduced to increase surface area.

Figure 10:
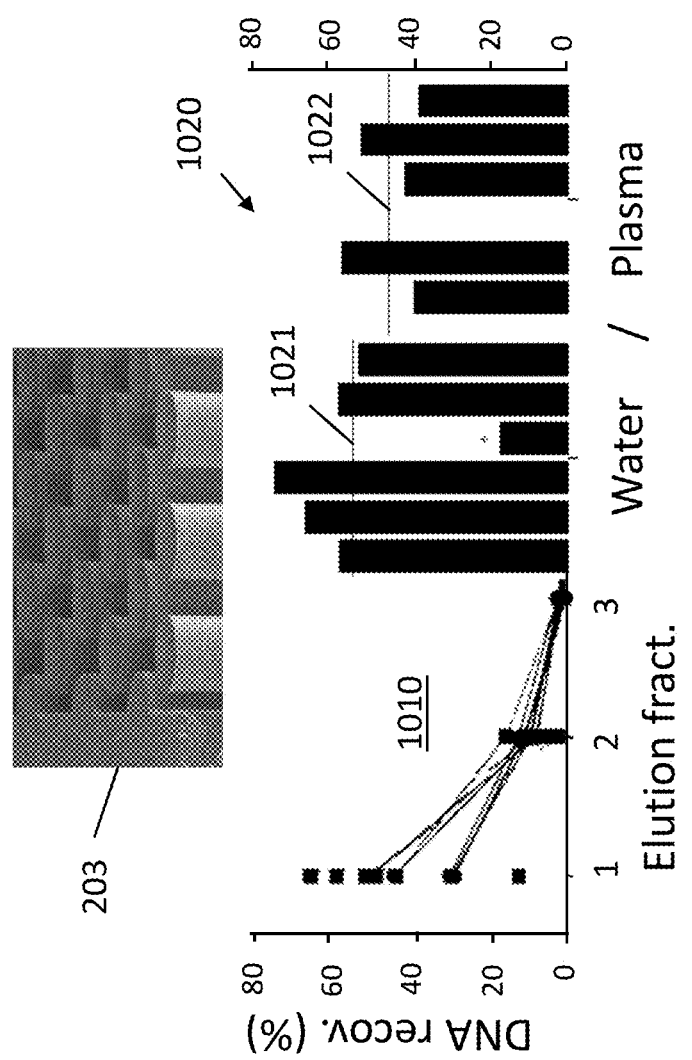
FIG. 10 illustrates the DNA recoveries of DNA in water and in plasma for a surface comprising silicon micropillars according to example embodiments of the present disclosure.

The DNA recoveries when a micropillar array 203 is included in the cavity, according to established DNA extraction and/or purification with LYS, AW1, AW2 and water, are shown in FIG. 10. The leftmost diagram 1010 shows the recovery according to elution fraction (only fractions between 1 and 2 are considered) for water (square graph points) and plasma (round graph points). The bar diagrams 1020 on the right of FIG. 10 show the recovery for water and plasma, respectively. The average recovery 1021 for water is 52.6% (not taking into account the result under 20%). The recovery 1022 for plasma is 44.1%.

Whereas in the above example reference is made to DNA, it is to be noted that this is similarly applicable to RNA or nucleic acids in general.

Figure 5:
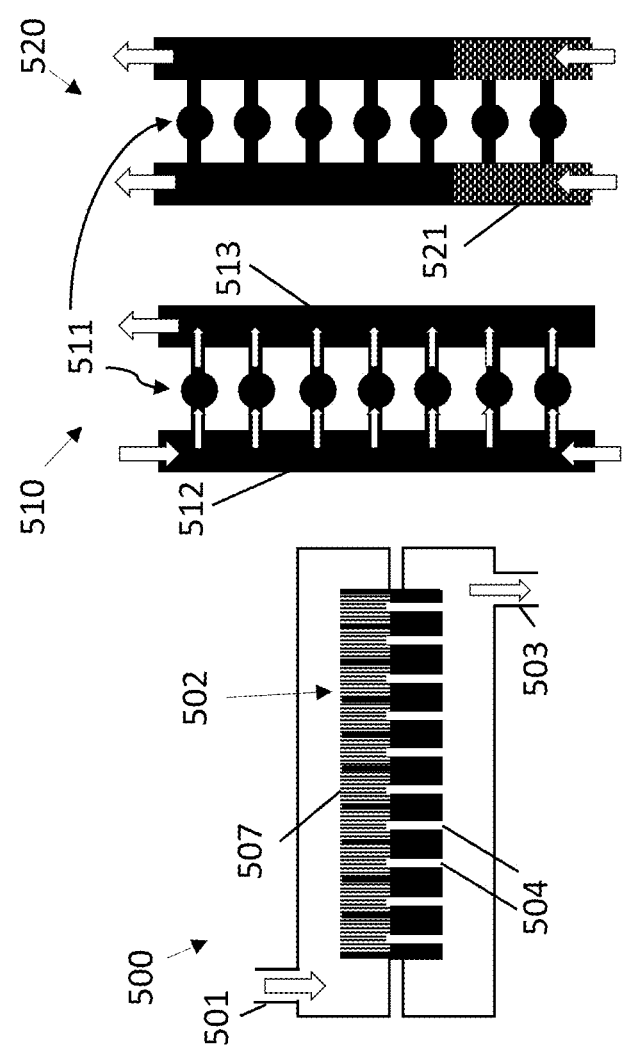
FIG. 5 illustrates different implementations (vertical and horizontal) of a platform according to example embodiments of the present disclosure for performing PCR.
Figure 11:
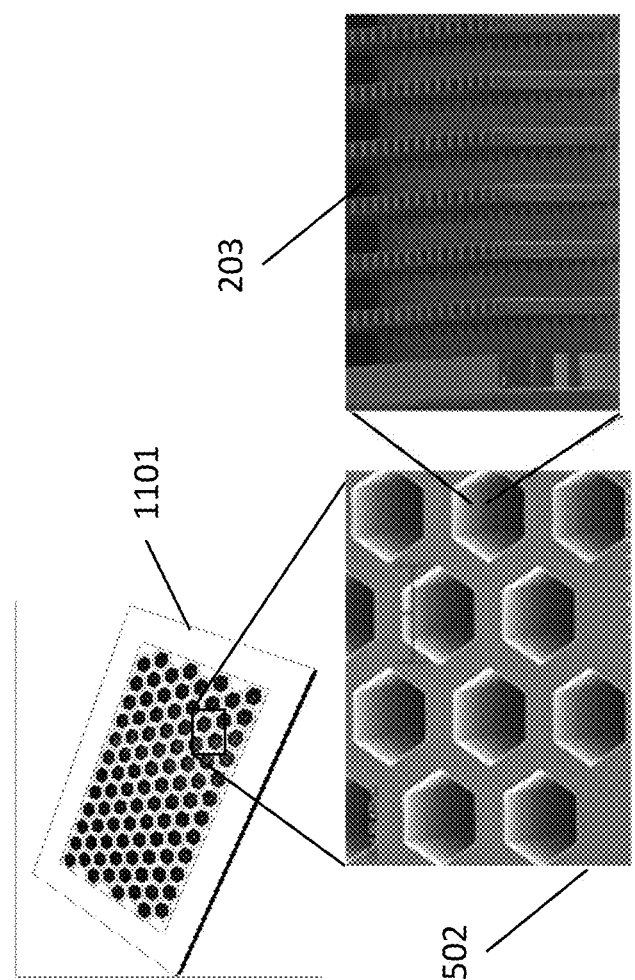
FIG. 11 illustrates an example of a cavity array for dPCR according to example embodiments of the present disclosure.

FIG. 11 shows an exemplary platform 1101 comprising an array 502 of hexagonal partitions 507 which can be vertically filled, as shown in the rightmost configuration 500 of FIG. 5. Each partition may comprise an array 203 of micropillars, which contribute to DNA extraction and/or purification.

Embodiments of the present disclosure may be used in genetic tests, screening, sequencing, oncology and antibiotic resistance studies, etc. In embodiments of the present disclosure, PCR on clinical or complex samples can be performed together with sample preparation. For example, a sample preparation step prior to dilution is not necessary. In some embodiments of the present disclosure, the bulk mix of DNA fragments can be traced back to their original genetic carrier, which was either very difficult or simply not possible in prior art techniques. Thus, combining PCR with extraction and/or purification in the partitions themselves has not only the advantage of time saving, but also the additional benefit that genetic targets from the same origin (i.e. same genetic carrier such as a cell, exosome, virus, bacteria, etc) will be physically constraint in the same cavity. As such, genetic correlation (linkage) (whereby the genetic fragments can be traced back to a single nucleic acid carrier) between different targets (e.g., target fragments of nucleic acid) can be easily obtained using a multiplex PCR. The present disclosure directly enables a plethora of applications that are very difficult or close to impossible to obtain with current state of the art methodologies. According to embodiments of the present disclosure, studies on differential gene expression (including detection of gene expression changes between single cells, or linking expression level of predetermined markers, e.g., mRNA, to single cell/entity) are possible, as well as single cell variant calling, which may help decreasing false positive and negative calling by studying the genetic make-up on single cells. It is also possible to introduce PCR adapters on single cell level using whole genome amplification techniques for sample preparation, as part of next-generation sequencing. The present disclosure is not limited to these applications, and embodiments can be used for studying single cell epigenetic markers.

Using standard state of the art technologies, nucleic acid extraction and/or purification is performed as a separate sample preparation step prior to amplification, so extraction and/or purification on such standard samples (containing, e.g., numerous cells) will yield a mix of nucleic acids. Starting from such a standard, prior art, sample, only bulk measurements can be performed and all information about targets originating from a nucleic acids carrier (e.g., a single cell, chromosome or genetic carrier) is lost. In contrast to these bulk measurements, with the proposed solution, genetic linkage or correlation between different DNA/RNA targets can be obtained directly.

Figure 12:
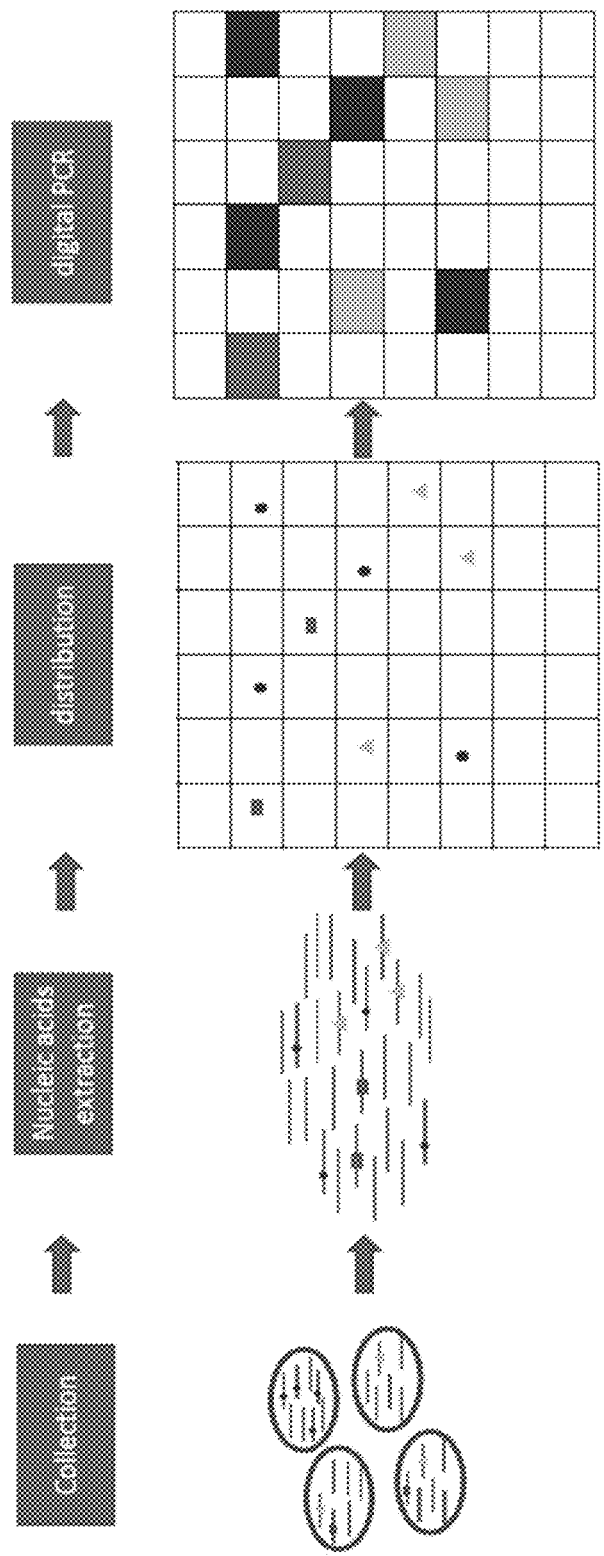
FIG. 12 illustrates the application of PCR according to an example embodiment of the present disclosure.
Figure 13:
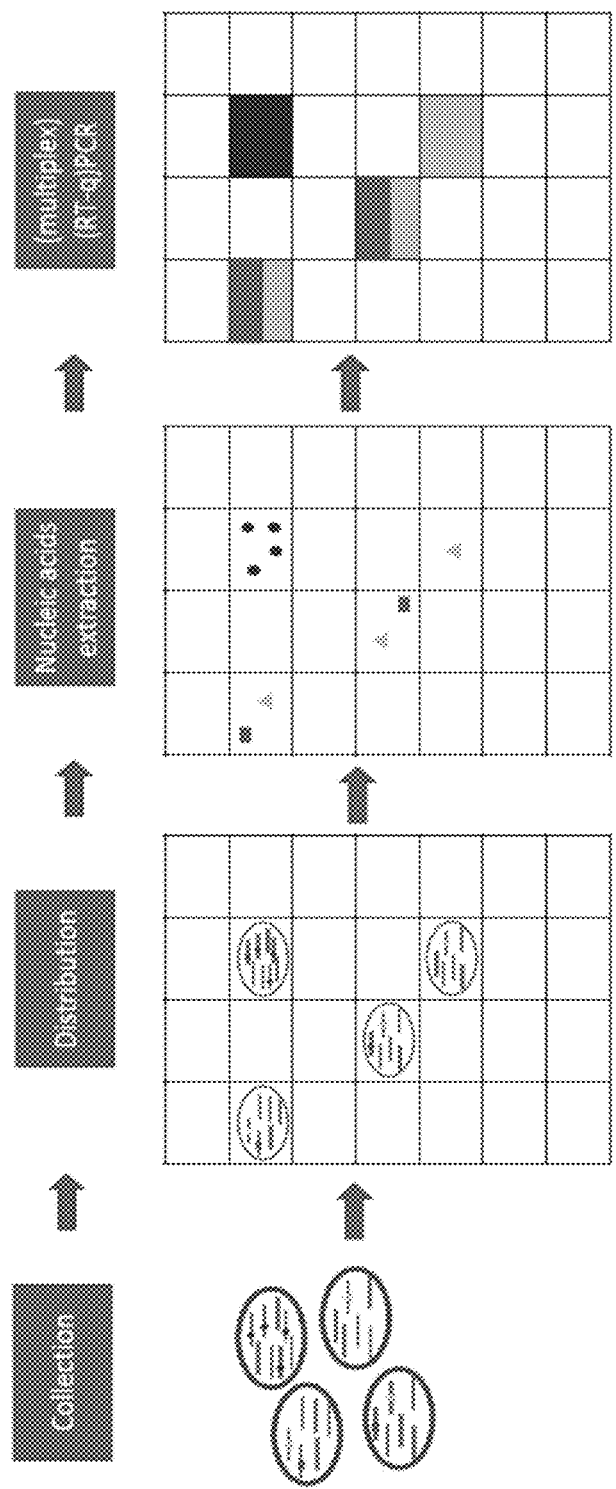
FIG. 13 illustrates the application of PCR whereby extraction and amplification is performed in the same cavity, illustrating advantages of an example embodiment of the present disclosure.
Figure 14:
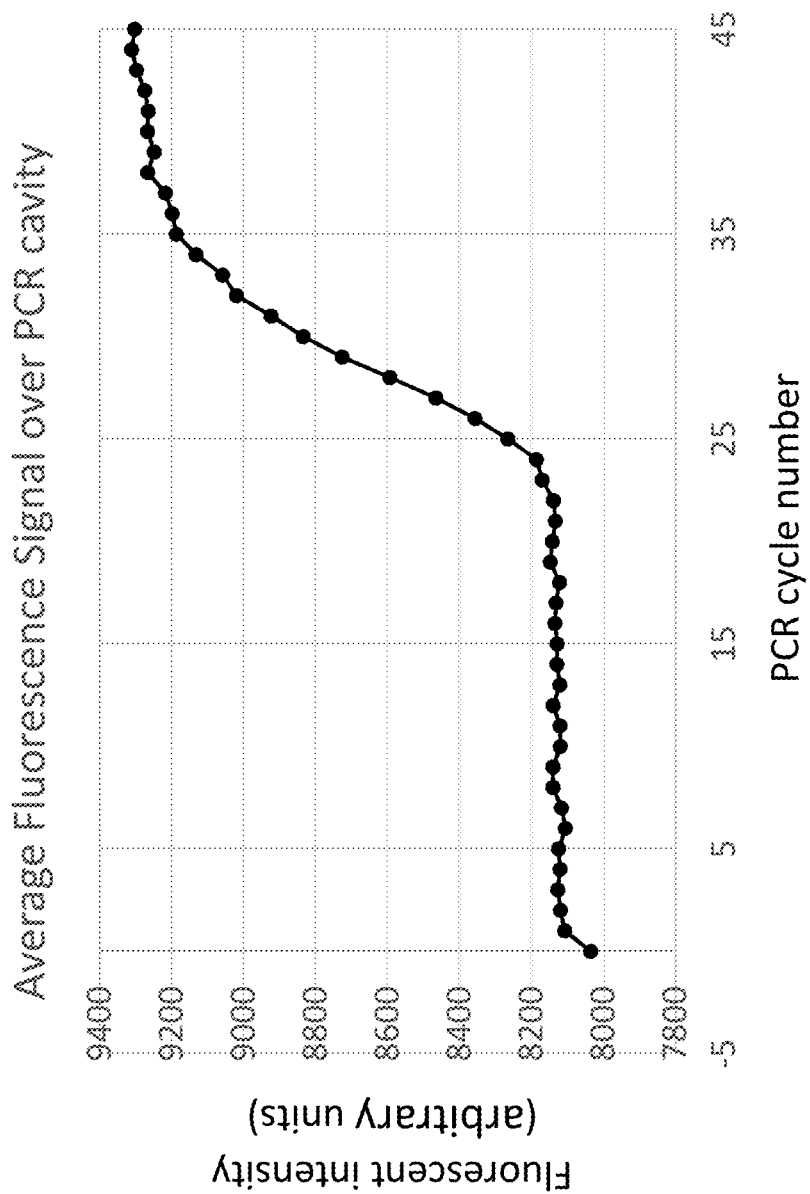
FIG. 14 shows an example result of extraction and amplification performed in a single cavity, using EGFR as target, illustrating an example embodiment of the present disclosure.

The latter is illustrated in FIG. 12 and FIG. 13, whereby FIG. 12 illustrates an exemplary situation whereby nucleic acid extraction is performed upfront, i.e., not in the same cavity as the cavity where the PCR is performed. FIG. 12 thus illustrates the collection of the sample, the step of nucleic acids extraction which is performed upfront but not in the same cavities as the cavities where PCR is performed, distribution of the extracted nucleic acids in the plurality of cavities, and the step of performing PCR. The method shown in FIG. 12 allows an absolute quantification but does not allow a linkage to the original bio-vesicle after PCR.

In FIG. 13 an exemplary method is described whereby the nucleic acids extraction is performed in the same cavity as the PCR amplification. The method comprises the steps of collecting the sample, performing a distribution of the sample over the plurality of cavities, performing the nucleic acids extraction in the plurality of cavities and performing PCR using the same plurality of cavities, so that there is a link between the marker and an individual bio-vesicle from which the nucleic acid is extracted. The method may therefore furthermore comprise a further characterization step of the bio-vesicles being present in the different cavities. Typical characterization methods that may be used therefore are microscopy (e.g., inverted microscopy, fluorescent microscopy, etc.), spectroscopy, or any other phenotypic screening method or assay. The method furthermore allows to observe a combined presence of certain markers per bio-vesicle and it allows observing differential expression between bio-vesicles.

In another example, DNA extraction from whole blood was performed using the reagents from Qiagen's DNeasy blood and tissue kit with silica micropillars in the extraction chip replacing the Qiagen silica spin column at a rate of 4 µl/min using a syringe pump. The 20 µl of blood lysate contained 3.2 µl of blood, proteinase K and AL (lysis) buffer with ethanol. Washing was performed with 8 µl of AW1 and 8 µl of AW2 wash buffers.

Figure 15:
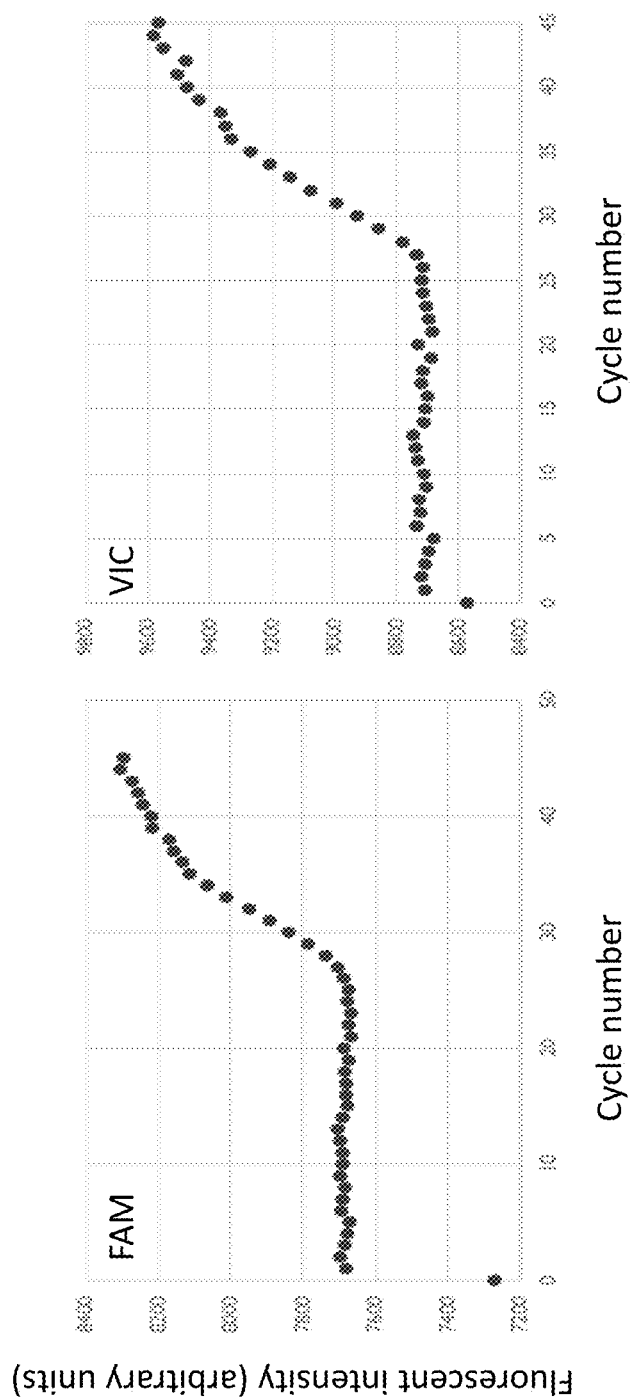
FIG. 15 shows an example result of extraction and amplification performed in a single cavity using SNP CYP2C9*2 as a target, illustrating an example embodiment of the present disclosure.

PCR master mix was prepared containing 2 µl ddPCR™ Supermix for Probes (No dUTP) (Biorad) and 0.2 µl EGFR probes and primers (Biorad). After an initial denaturation for 5 min at 95° C., 45 PCR cycles were run (95° C.-15 sec; 60° C.-45 sec). Ramp rate for cooling was 6 seconds, for heating 12 seconds for a total run time of 63.5 minutes. The qPCR result for combined extraction and PCR is shown in the graph of FIG. 15, illustrating the possibility of combined extraction and quantitative PCR in a single cavity.

In still another example, DNA extraction from whole blood was performed using the reagents from Qiagen's DNeasy blood and tissue kit with silica micropillars in the extraction chip replacing the Qiagen silica spin column at a rate of 4 µl/min using a syringe pump. The 20 µl of blood lysate contained 3.2 µl of blood, proteinase K and AL (lysis) buffer with ethanol. Washing was performed with 8 µl of AW1 and 8 µl of AW2 wash buffers.

PCR master mix was prepared containing Amplitaq polymerase in Amplitaq buffer with BSA (Thermo Fisher), BSA (5 mg/µl), dNTP (10 mM each), and primers and probes for SNP CYP2C9*2. After an initial denaturation of 1 min at 95° C., 33 PCR cycles were run (95° C.-5 sec; 60° C.-5 sec; 68° C.-3 sec). The ramp time for cooling was 2 seconds, for heating 7 seconds, for a total run time of 21 min.

The qPCR result for combined extraction and multiplex PCR is shown in the graph. Amplification in both FAM as well as VIC dye channels was observed in agreement with characteristics of embodiments of the present disclosure.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. A method for analyzing a fluid sample, the method comprising:
inserting a fluid sample into a first fluid reservoir of a substrate and buffers or reagents into a second fluid reservoir of the substrate, wherein the first fluid reservoir and the second fluid reservoir are fluidly coupled to a first end of a meandering microfluidic channel that is fluidly coupled on a second end to at least one cavity of the substrate, wherein the fluid sample and the buffers or reagents mix together as they pass through the meandering microfluidic channel and into the at least one cavity;
performing nucleic acid extraction or purification in the cavity; and
subsequently performing nucleic acid amplification in the cavity, wherein the cavity comprises a silicon-based pillar filter.

2. The method of claim 1, wherein the silicon-based pillar filter comprises a plurality of micropillar structures.

3. The method of claim 1, wherein the silicon-based pillar filter comprises silicon pillars.

4. The method of claim 1, further comprising dividing the fluid sample over a multitude of cavities.

5. The method of claim 1, further comprising performing nucleic acid amplification after performing nucleic acid extraction without performing an elution step in between.

6. The method of claim 1, wherein the second end of the meandering microfluidic channel is fluidly coupled to a plurality of cavities, wherein the method further comprises performing, for each cavity, nucleic acid extraction in the cavity and consequently performing nucleic acid amplification in the cavity.

7. The method of claim 1, wherein the second end of the meandering microfluidic channel is fluidly coupled to a plurality of cavities, wherein the method further comprises:
for each cavity, performing nucleic acid extraction in the cavity and subsequently performing nucleic acid amplification in the cavity, and
applying a digital PCR analysis for the plurality of cavities for determining a concentration of a target in the fluid sample.

8. The method of claim 6, further comprising providing a predetermined volume of fluid containing nucleic acid carriers per cavity, for obtaining an average of less than a nucleic acid carrier per cavity.

9. The method of claim 8, further comprising providing a volume of less than 10 nanoliters per cavity.

10. A microfluidics system for analyzing a fluid sample, the microfluidics system comprising:
a substrate comprising:
a first fluid reservoir configured to receive the fluid sample;
a second fluid reservoir configured to receive buffers or reagents;
a meandering microfluidic channel having a first end that is fluidly coupled to the first fluid reservoir and the second fluid reservoir, wherein the meandering microfluidic channel facilitates mixing of the fluid sample and the buffers or reagents as the fluid sample and the buffers or reagents pass through the meandering microfluidic channel; and
at least one cavity fluidly coupled to a second end of the meandering microfluidic channel, wherein the at least one cavity comprises a surface configured to facilitate nucleic acid extraction, and a silicon-based pillar filter; and a controller configured to control conditions of the cavity to facilitate nucleic acid extraction in the cavity and to subsequently control conditions of the cavity to facilitate nucleic acid amplification within the cavity.

11. The microfluidics system of claim 10, wherein the silicon-based pillar filter comprises a plurality of micropillar structures.

12. The microfluidics system of claim 10, wherein the silicon-based pillar filter comprises silicon pillars.

13. The microfluidics system of claim 10, wherein the controller is configured to facilitate performance of nucleic acid amplification after performance of nucleic acid extraction without performing an elution step in between.

14. The microfluidics system of claim 10, wherein the second end of the meandering microfluidic channel is fluidly coupled to a plurality of cavities and wherein the controller is configured to induce nucleic acid extraction and subsequently nucleic acid amplification in each of the cavities.

15. The microfluidics system of claim 14, wherein the microfluidics system further comprises a processor configured to perform a digital PCR analysis based on the plurality of cavities.

16. The microfluidics system of claim 14, wherein each of the plurality of cavities has a maximum capacity of 10 nL.

17. The microfluidics system of claim 10, wherein the microfluidics surface of the at least one cavity comprises silicon oxide or wherein the substrate comprises at least one trench for thermally isolating the at least one cavity.

18. The microfluidics system of claim 10, wherein the system is further configured to provide capillary pumping, comprises a mixer for mixing buffers or reagents, or comprises a heater for adjusting a temperature of the cavity.

19. A diagnostic device comprising the microfluidics system of claim 10, the diagnostic device being a lab-on-chip device.

20. A polymerase chain reaction (PCR) method comprising:
    inserting into a microfluidics system a fluid sample and one or more buffers or reagents, wherein the microfluidics system comprises:
        a substrate comprising:
            a first fluid reservoir configured to receive the fluid sample;
            a second fluid reservoir configured to receive the buffers or reagents;
            a meandering microfluidic channel having a first end that is fluidly coupled to the first fluid reservoir and the second fluid reservoir, wherein the meandering microfluidic channel facilitates mixing of the fluid sample and the buffers or reagents as the fluid sample and the buffers or reagents pass through the meandering microfluidic channel; and
            at least one cavity fluidly coupled to a second end of the meandering microfluidic channel, wherein the at least one cavity comprises a surface configured to facilitate nucleic acid extraction, and a silicon-based pillar filter; and
        a controller configured to control conditions of the cavity to facilitate nucleic acid extraction in the cavity and to subsequently control conditions of the cavity to facilitate nucleic acid amplification within the cavity;
    extracting nucleic acid from the at least one cavity; and
    processing the extracted nucleic acid to screen for antibiotic resistance, identify relative changes in gene expression, or link multiple nucleic acids targets to a single genetic carrier.

* * * * *